(12) United States Patent
Arthur et al.

(10) Patent No.: US 10,206,740 B2
(45) Date of Patent: Feb. 19, 2019

(54) EXPANDABLE CANNULA AND METHOD OF USE

(71) Applicant: KYPHON SARL, Neuchatel (CH)

(72) Inventors: Amy L. Arthur, San Jose, CA (US); Mojan Goshayeshgar, Atherton, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 364 days.

(21) Appl. No.: 15/005,316

(22) Filed: Jan. 25, 2016

(65) Prior Publication Data

US 2016/0135877 A1 May 19, 2016

Related U.S. Application Data

(62) Division of application No. 13/798,707, filed on Mar. 13, 2013, now Pat. No. 9,271,750.

(51) Int. Cl.

| | |
|---|---|
| *A61B 17/32* | (2006.01) |
| *A61B 18/14* | (2006.01) |
| *A61B 17/34* | (2006.01) |
| *A61B 18/04* | (2006.01) |
| *A61B 17/16* | (2006.01) |
| *A61B 17/3209* | (2006.01) |
| *A61B 17/00* | (2006.01) |
| *A61B 18/00* | (2006.01) |
| *A61B 18/12* | (2006.01) |

(52) U.S. Cl.
CPC ...... *A61B 18/1487* (2013.01); *A61B 17/1615* (2013.01); *A61B 17/3209* (2013.01); *A61B 17/320016* (2013.01); *A61B 17/3439* (2013.01); *A61B 18/042* (2013.01); *A61B 2017/0073* (2013.01); *A61B 2018/00434* (2013.01); *A61B 2018/00601* (2013.01); *A61B 2018/1213* (2013.01)

(58) Field of Classification Search
CPC ............ A61B 17/3209; A61B 17/3421; A61B 17/3423; A61B 17/3431; A61B 17/3433; A61B 17/3439; A61B 18/1487
See application file for complete search history.

(56) References Cited

U.S. PATENT DOCUMENTS

| | | |
|---|---|---|
| 5,158,545 A | 10/1992 | Trudell et al. |
| 5,286,253 A | 2/1994 | Fucci |
| 5,370,651 A | 12/1994 | Summers |
| 5,540,693 A | 7/1996 | Fisher |
| 5,769,086 A | 6/1998 | Ritchart et al. |
| 5,810,806 A | 9/1998 | Ritchart et al. |
| 5,814,058 A | 9/1998 | Carlson et al. |
| 6,090,072 A | 7/2000 | Kratoska et al. |
| 7,033,357 B2 | 4/2006 | Baxter et al. |
| 7,347,857 B2 | 3/2008 | Anderson et al. |
| 7,488,295 B2 | 2/2009 | Burbank et al. |

(Continued)

*Primary Examiner* — Allen Porter, Jr.

(57) ABSTRACT

A cutting device includes an elongated shaft that extends between a proximal end and a distal end. A distal arm extends from the distal end of the elongated shaft. The distal arm includes an inner surface defining a cavity and an outer surface defining a blunt tip. At least one proximal arm extends from the distal end of the elongated shaft at a position proximal to the distal arm. The at least one proximal arm having an inner surface defines a cavity including a cutting portion configured to cut tissue.

18 Claims, 3 Drawing Sheets

(56) References Cited

U.S. PATENT DOCUMENTS

| | | |
|---|---|---|
| 7,967,776 B2 | 6/2011 | Von Segesser |
| 2003/0023239 A1 | 1/2003 | Burbank et al. |
| 2003/0050638 A1 | 3/2003 | Yachia et al. |
| 2005/0090852 A1* | 4/2005 | Layne ................ A61B 17/3417 606/190 |
| 2008/0009826 A1* | 1/2008 | Miller ................ A61B 17/3478 604/508 |
| 2008/0154304 A1 | 6/2008 | Crawford et al. |
| 2011/0071429 A1* | 3/2011 | Weisman ........... A61B 10/0283 600/566 |
| 2011/0144661 A1* | 6/2011 | Houser .............. A61B 17/0057 606/142 |
| 2012/0016192 A1 | 1/2012 | Jansen et al. |
| 2012/0172668 A1 | 7/2012 | Kerns et al. |
| 2012/0271357 A1 | 10/2012 | Arthur et al. |

\* cited by examiner

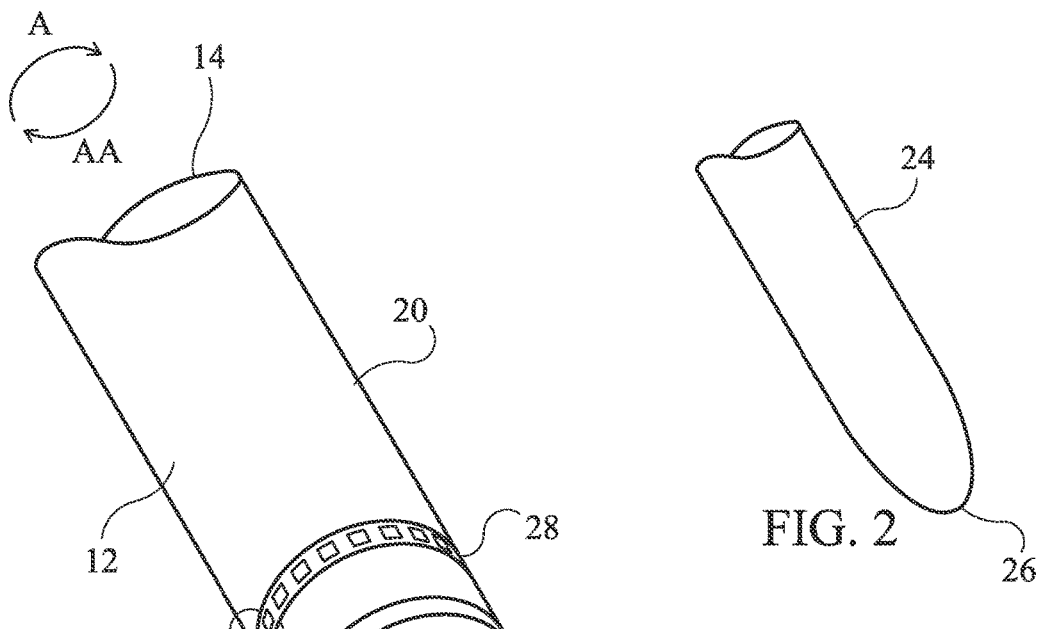
FIG. 1
FIG. 2
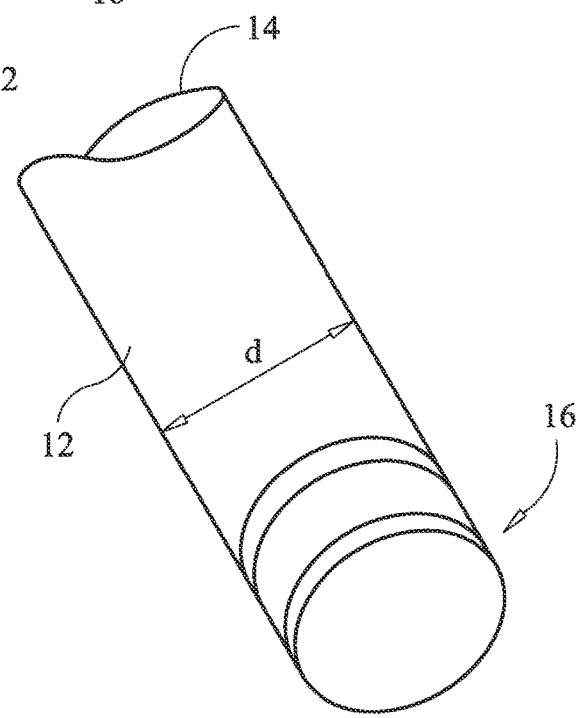
FIG. 3

EXPANDABLE CANNULA AND METHOD OF USE

CROSS-REFERENCE TO RELATED APPLICATIONS

This application is a Divisional of U.S. patent application Ser. No. 13/798,707, filed on Mar. 13, 2013, which is incorporated herein by reference herein, in its entirety.

FIELD OF THE INVENTION

The present invention relates generally to devices and methods for a surgical tool for creating access to and/or cutting a material or substance. More specifically, the devices and methods are useful for resecting nerve and/or soft tissue via a minimally invasive procedure to alleviate pain.

BACKGROUND

Standard methods of cutting tissue may include using a scalpel, scissors, and radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has re-insufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices are wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Another problem with currently available RF nerve ablation devices is that they attempt to destroy nerve tissue from a central location including the tip of the device and a 3-D spherical or cylindrical zone around it. As a result, the further away the resecting ability is from the central zone the less effective the nerve destruction. Consequently, often the nerve is not adequately ablated leading to continued pain symptoms.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Other devices such as mechanical rongeurs can be used to remove soft tissue. However, these devices require the insertion of relatively large cannulas that further complicate the surgical procedure and can cause nerve compression and pain with variable clinical efficacy.

Accordingly, there is a need for devices and methods to provide efficient severing or cutting of nerve and/or soft tissue that can be used during a minimally invasive procedure and/or during an open surgical procedure. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY OF THE INVENTION

This application is directed to a surgical device for enlarging the diameter of a hole in tissue. The surgical device includes an elongated shaft extending between a proximal end and a distal end and including an outer surface. A stylet is disposed within the elongated shaft. The stylet is configured to retractably extend out of the elongated shaft so as to contact tissue. A cutting portion is disposed on a portion of the outer surface of the elongated shaft. The cutting portion is configured to cut tissue as the shaft is inserted into the tissue so as to enlarge the diameter of the hole in the tissue. In one embodiment, the cutting portion can also be a heating portion designed to cut tissue such that the tissue does not reapproximate its previous position after a working cannula is removed.

In one embodiment, a device for expanding a diameter of a hole in tissue is provided. The device includes an elongated shaft extending between a proximal end and a distal end and including a first portion and a second portion extending parallel to the first portion. A rod disposed within the elongated shaft, the rod being configured to retractably expand the elongated shaft such that the first portion and the second portion from a first collapsed orientation such that the first and second portion are disposed adjacent to each other to a second expanded orientation such that the first and second portion are disposed at a distance from each other so as to enlarge the hole in the tissue.

In one embodiment, a method of using a device to enlarge a hole in tissue comprising cutting a hole in the tissue is provided. A cannula is inserted into or on the anatomy of a patient. The cannula comprises an elongated shaft extending between a proximal end and a distal end and including a first portion and a second portion extending parallel to the first portion. A rod is disposed within the elongated shaft, the rod being configured to retractably expand the elongated shaft such that the first portion and the second portion from a first collapsed orientation such that the first and second portion are disposed adjacent to each other to a second expanded orientation such that the first and second portion are disposed at a distance from each other so as to enlarge the hole in the tissue. The rod is manipulated by a medical practitioner to expand the first and second portion to the expanded orientation to expand the hole in the tissue. In the alternative, cannulas that do not expand but are sequentially larger in diameter may be used to increase the size of the working/hole in the tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1 is a perspective view of an embodiment of the device in accordance with the principles of the present disclosure;

FIG. 2 is perspective view of components of the device shown in FIG. 1;

FIG. 3 is a perspective view of an embodiment of the device in accordance with the principles of the present disclosure;

DETAILED DESCRIPTION OF THE INVENTION

Figure 4:
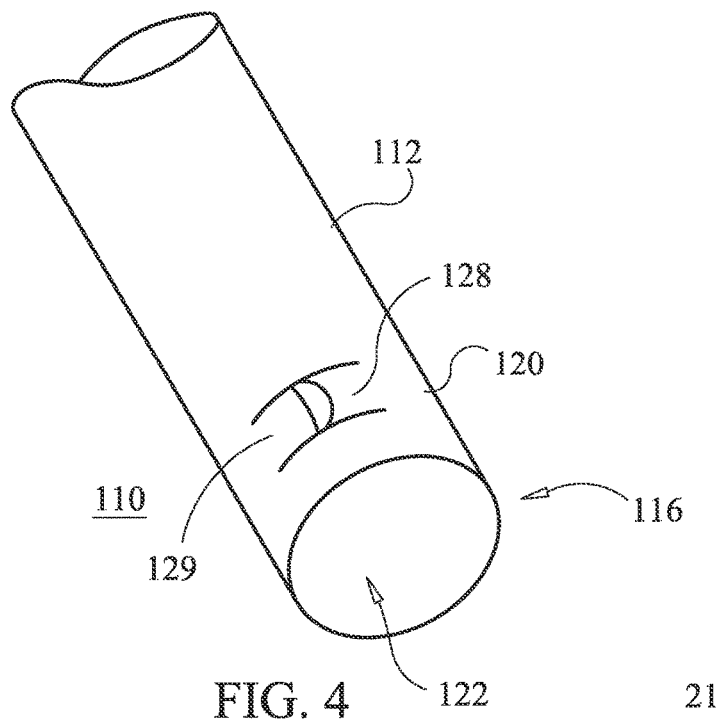
FIG. 4 is a perspective view of an embodiment of the device in accordance with the principles of the present disclosure.

Devices for efficient severing or cutting of a material or substance such as nerve, soft tissue and/or bone suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided and may be beneficial.

In one embodiment, a blunt stylet is nested within a cannula to penetrate soft tissue. An outer wall of the cannula has ring of exposed metal to deliver RF energy to contact soft tissue. The tissue may either be cut or heated. The remaining portion of outer wall of the cannula is insulated. In one embodiment, successive cannulas may be placed over the stylet to increase the size of a hole in the soft tissue.

In one embodiment, the cannula has single or multiple rasps or grater-like openings on the side wall. The rasp opening is configured to cut and enlarge a bony opening. The cannula is twisted about its axis to shave bone. The bony fragments are collected in the cannula lumen and may be evacuated via suction or with mechanical method, such as an auger.

In one embodiment, the cannula is created from two halves of tubing. Each tubing half has ratchet feature that mates with corresponding ratchet feature in other tubing half. An expandable stylet is placed in cannula lumen to increase cannula diameter and separate the first half form the second half.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

For purposes of the description contained herein, "vacuum" means pressure within a space that is lower by any amount than atmospheric or ambient pressure, and although not exclusive of a condition of absolute vacuum defined by a complete absence within a space of air, fluid or other matter, the term as used herein is not meant to require or be limited to such a condition.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Radiofrequency (RF) ablation devices have been available to surgeons to treat many medical conditions, for example, in the treatment of tumors in lung, liver, kidney, bone and other body organs. Pulsed RF has also been used for treatment of tumors, cardiac arrhythmias, chronic and post-operative pain, bone fracture and soft tissue wounds.

The components of the cutting device can be fabricated from biologically acceptable materials suitable for medical apparatuses, including metals, synthetic polymers, ceramics, thermoplastic and polymeric material and/or their composites. For example, the components of the holding device, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

Various components of the holding device may have material composites, including the above materials, to achieve various desired characteristics such as strength, rigidity, elasticity, compliance, and biomechanical performance, durability and to provide a non-stick surface. The components of the holding device may be monolithically formed, extruded, coextruded, hot molded, cold molded, press molded, integrally connected or include fastening elements and/or coupling components, as described herein.

In one embodiment, as shown in FIGS. 1-3, device 10, in accordance with the present disclosure, includes an elongated shaft 12. Shaft 12 extends between a proximal end 14 and a distal end 16. Shaft 12 includes an inner surface 18 and an outer surface 20. Inner surface 18 defines a passageway 22. It is envisioned that all or only a portion of shaft 12 may have various cross section configurations, such as, for example, cylindrical, flat, oval, oblong, triangular, square, polygonal, irregular, uniform, non-uniform, offset, staggered, undulating, arcuate, variable and/or tapered. It is contemplated that surfaces 18, 20 includes various surface configurations, such as, for example, smooth, rough, mesh, porous, semi-porous, dimpled and/or textured. In various embodiments, the navigational sources can be coupled with pre-procedure imaging means such as for example, CT, MRI, PET scan, etc. so that the target nerve or soft tissue to be cut can be identified and accurately located during the procedure. In some embodiments, shaft 12 can be operatively connected to semi-steerable or navigational sources for easier guidance into tissue. A stylet 24 is configured for retractable placement into and through passageway 22 of shaft 12 such that a distal end 26 extends past distal end 16 of shaft 12 to contact tissue.

A cutting portion, such as, for example, a cutting band 28 is disposed around surface 20. In one embodiment, cutting band 28 includes electrodes 30 configured to emit a RF frequency adapted for cutting nerve and/or soft tissue. In one embodiment, cutting band 28 is configured to emit pulsed plasma signals adapted for cutting nerve and/or soft tissue. In one embodiment, device 10 includes an electrically insulated layer adjacent to and exposing cutting band 28 such that the energy transmitted from the RF frequency and/or the plasma is centralized at cutting band 28. In some embodiments, the coating or insulating layer can be glass or ceramic having a thickness from about 0.005 to about 0.5 mm thick or from about 0.01 to about 0.2 mm thick. By rotating shaft 12 back and/or forth the RF or plasma signals will cut the tissue and enlarge the hole in the tissue. In one embodiment, the ring extends around either the majority of the entire circumference or the entire circumference of the cannula so that the cannula does not have to be rotated.

In one embodiment, shaft 12 includes a connection to engage a vacuum (not shown) to remove the resected nerve and/or soft tissue. Alternatively, an additional channel is possible for delivering fluid to the surgical site. At its proximate end, shaft 12 can be operatively connected to the vacuum for providing suction to resected nerve and/or tissue. A vacuum line may be used to transmit vacuum from a vacuum source (not shown) to a receiving aperture connected to shaft 12. The vacuum is in communication with opening 22 such that as tissue is resected from a target area, the tissue will be removed via suction. The vacuum may be provided inside opening 22 or, alternatively, may be provided through an additional lumen separate from opening 22. Any suitable aspirator, cylindrical or otherwise, or other mechanism that creates vacuum upon the movement of an actuating member thereof, may be utilized as a vacuum source, such as, for example, a syringe or mechanical vacuum.

The present disclosure also provides methods for cutting or resecting nerve and/or soft tissue. The methods comprise positioning a distal region of shaft 12 of device 10 within a hole in tissue. Distal end 16 is positioned at the area where the tissue enlarged. To enlarge the diameter of the hole, shaft 12 is rotated back and forth, shown by arrows A and AA, such that cutting band 28 burns or cuts the tissue to enlarge the hole. In the alternative, a larger cannula is inserted in order to increase the diameter.

In one embodiment, a diameter d increases from distal end 16 to proximal end 14 such that movement of shaft 12 into the hole allows the larger diameter portion of shaft 12 to enlarge the hole. In one embodiment, increased diameter shafts 12 can be placed over a smaller diameter shaft such that the hole is enlarged as the increased diameter shaft is placed over the smaller diameter shaft.

In one embodiment, as shown in FIG. 4, shaft 112 includes a cutting portion 128 that includes a rasp or grater-like cutting opening 129. As shaft 112 is rotated the rasp opening 129 cuts or shaves tissue to enlarge the hole. Cut tissue fragments are collected in passageway 122 of shaft 112. Rasp opening 129 is sharp so as to facilitate cutting of bone tissue. The vacuum within or outside of shaft 12 is utilized to remove the cut nerve, soft tissue, and/or bone tissue such that device 10 can be reinserted for additional cutting.

The present disclosure provides for a method for cutting or resecting bone tissue using surgical device 110. Distal end 116 is positioned in a hole at a predetermined target area by a medical practitioner. In various embodiments, navigational sources can be coupled with pre-procedure imaging means such as for example, CT, MRI, PET scan, etc. so that the target nerve or soft tissue to be cut can be identified and accurately located during the procedure. Once distal end 116 is positioned at a targeted hole on a bone that is to be enlarged, shaft 112 is rotated in a circular motion such that rasp opening 129 cuts evenly and circumferentially to enlarge the hole in the bone tissue. A vacuum within or outside of shaft 112 is utilized to remove the cut nerve, soft tissue, and/or bone tissue such that device 110 can be reinserted for additional cutting.

Figure 5:
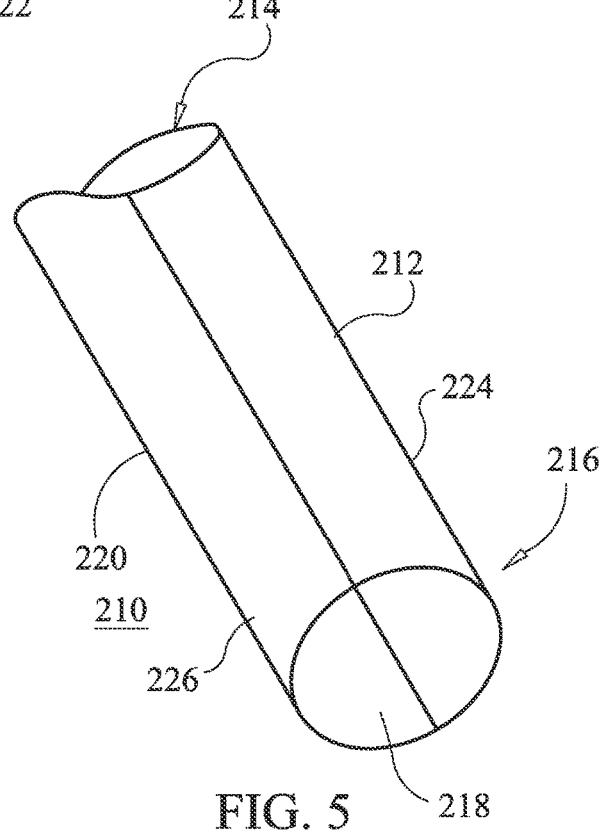
FIG. 5 is a perspective view of an embodiment of the device in accordance with the principles of the present disclosure.
Figure 6:
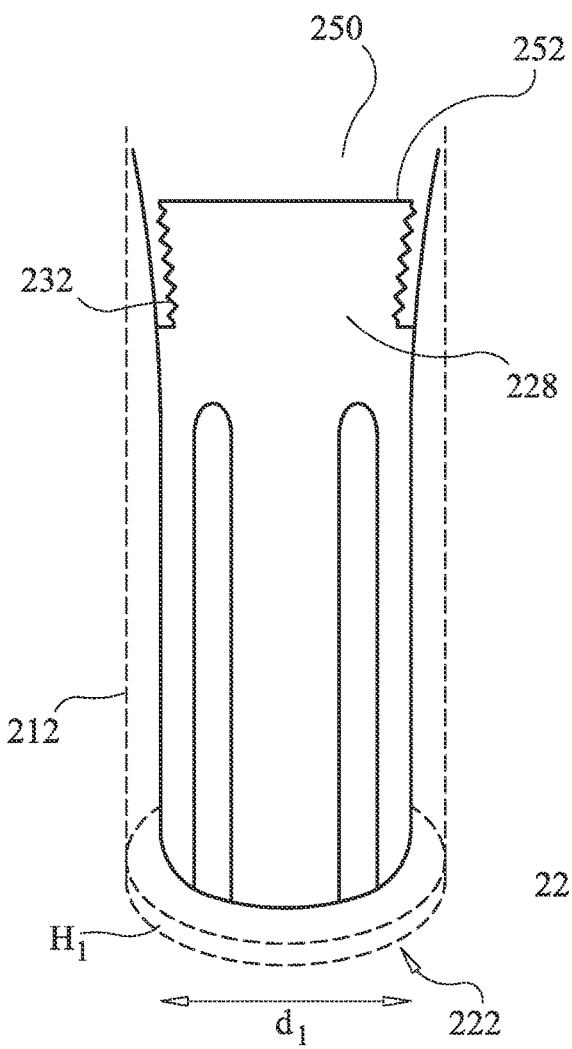
FIG. 6 is a side view of an embodiment of the device in accordance with the principles of the present disclosure.
Figure 7:
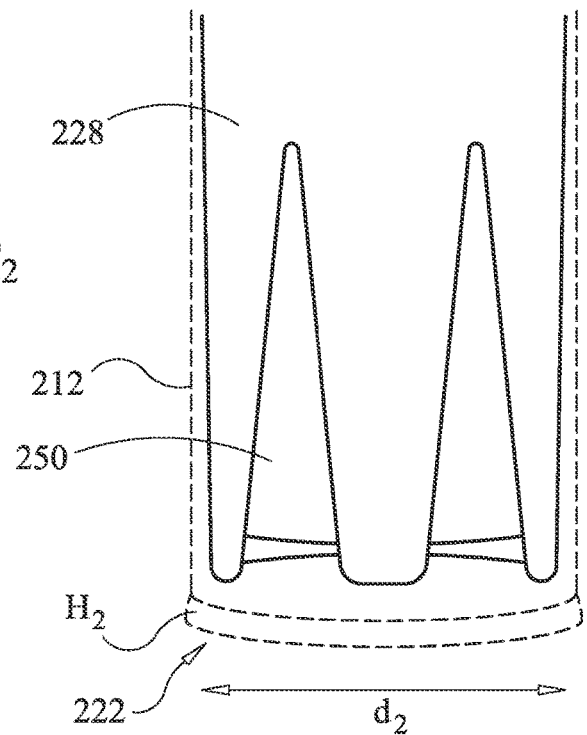
FIG. 7 is a cross section view of components of the device shown in FIG. 6.

In one embodiment, as shown in FIGS. 5-7, shaft 212 extends between a proximal end 214 and a distal end 216. Shaft 212 includes an inner surface 218 and an outer surface 220. Inner surface 218 defines a passageway 222. Shaft 212 includes at least two portions, such as, for example, a first portion 224 and a second portion 226. Portions 224, 226 are configured to retractably expand shaft 212 such that portion 224 and portion 226 move from a first collapsed orientation in which the first and second portion are disposed adjacent to each other, to a second expanded orientation in which the first and second portion are disposed at a distance from each other so as to enlarge the hole in the tissue.

An expandable stylet 228 is configured to be placed within shaft 212 such that expansion of stylet 228 causes expansion of shaft 212. Stylet 228 is configured for retractable placement into and through passageway 222 of shaft 212 such that as stylet 228 moves through passageway 222, stylet 228 expands shaft 212 by pushing portions 224 and 226 away from each other in the direction shown by arrow B. In one embodiment, a rod 250 is engaged with stylet 228 by a ratchet mechanism or as shown, a threaded outer surface 252 of rod 250. Inner surface 230 of stylet 228 includes a threaded surface 232 configured for engagement with threaded surface 252. As rod 250 translates through stylet 228, threaded surface 252 engages threaded surface 232 to expand stylet 228 and portions 224, 226, as shown in FIG. 7. As such, shaft 212 inserted within hole H has an initial diameter of d1, as shaft 212 expands, hole H and shaft 212 are enlarged to a diameter d2, wherein d2 is large than d1. Threaded surfaces 252 and 232 allow for incremental enlargement of hole H so as to enlarge hole H slowly to prevent damage to the tissue.

In one embodiment, shaft 12 is operatively coupled to a source of navigational capability to allow easier pushing through the tissues. In various embodiments, the methods of cutting disclosed herein can include a pre-procedure step wherein the probe or needle can be coupled to a CT or MRI machine so that the target nerve and/or soft tissue to be cut can be identified and accurately located during the resection procedure.

The methods for cutting described hereinabove allow complete resection of the nerve avoiding the problems and partial effectiveness of current RF and cryoablation devices available in the art, and also allow for easier, more efficient, more complete, and safer removal of soft tissue that is causing stenosis pain symptoms.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A cannula for expanding a diameter of a hole in tissue:
an elongated shaft having a proximal end and a distal end,
the elongated shaft including a passageway extending therethrough, and the elongated shaft including adjacent the distal end thereof a first portion and a second portion extending parallel to one another, the first portion and the second portion each having an inner wall portion, the first portion and the second portion being moveable with respect to one another between a unexpanded first position and an expanded second position, and the first portion and the second portion defining a first diameter in the unexpanded first position;

an expandable stylet disposed within the passageway of the elongated shaft, the expandable stylet having a proximal end and a distal end, the expandable stylet including adjacent the distal end thereof an expandable end portion and a first outer surface formed on the expandable end portion, and the expandable end portion being moveable between an unexpanded third position and an expanded fourth position; and a rod disposed within the elongated shaft, the rod being configured to engage the proximal end of the expandable stylet and translate through the elongated shaft to expand the expandable end portion of the expandable stylet from the unexpanded third position to the expanded fourth position;

wherein, during expansion of the expandable stylet, the first outer surface of the end portion contacts the inner wall portions of the first portion and the second portion of the elongated shaft to move the first portion and the second portion from the unexpanded first position to the expanded second position, the first portion and the second portion defining a second diameter in the expanded second configuration, the second diameter being greater than the first diameter;

and wherein, when the cannula is positioned in the hole in the tissue, movement of the first portion and the second portion of the elongated shaft from the unexpanded first position to the expanded second position enlarges the hole in the tissue.

2. The cannula of claim 1, wherein the rod is threadably engaged with an inner surface of the expandable stylet such that translation of the rod through the elongated shaft causes expansion of the end portion of the stylet and corresponding expansion of the first portion and the second portion of the elongated shaft.

3. The cannula of claim 1, wherein the rod and the expandable stylet include a ratcheting connection such that the first portion and the second portion can be incrementally expanded so as to expand the hole in the tissue.

4. The cannula of claim 1, wherein the rod is hollow and the elongated shaft further includes an attachment to a vacuum to produce suction to remove tissue captured in the elongated shaft.

5. The cannula of claim 1, wherein the elongated shaft is configured to receive a surgical tool.

6. The cannula of claim 1, wherein the end portion of the expandable stylet includes at least a first portion and a second portion spaced apart from one another, and, during expansion of the expandable stylet, the first portion and the second portion of the end portion move farther apart from one another.

7. The cannula of claim 1, wherein the end portion of the expandable stylet includes at least a first portion and second portion, the first portion and the second portion of the end portion are spaced apart a maximum first distance when the end portion is in the unexpanded third position, and the first portion and the second portion of the end portion are spaced apart a maximum second distance when the end portion is in the expanded fourth position, the maximum second distance being greater than the maximum first distance.

8. The cannula of claim 1, wherein the elongated shaft includes adjacent the distal end thereof a second outer surface and a cutting portion provided on the second outer surface, the cutting portion being configured to cut the tissue.

9. The cannula of claim 8, wherein the cutting portion includes a band extending at least partially around the outer surface of the elongated shaft, the band including a plurality of spaced apart openings.

10. The cannula of claim 8, wherein the cutting portion includes a rasp surface configured to cut the tissue, and wherein rotation of the elongated shaft causes the rasp to cut the tissue.

11. A method of using a device to enlarge a hole in tissue comprising:

cutting a hole in the tissue;

inserting a portion of a cannula into the hole in the tissue, the cannula comprising an elongated shaft having a proximal end and a distal end, the elongated shaft including a passageway extending therethrough, and the elongated shaft including adjacent the distal end thereof a first portion and a second portion extending parallel to one another, the first portion and the second portion each having an inner wall portion; an expandable stylet disposed within the passageway of the elongated shaft, the expandable stylet having a proximal end and a distal end, the expandable stylet including adjacent the distal end thereof an expandable end portion and a first outer surface formed on the expandable end portion; and a rod disposed within the elongated shaft, the rod being configured to engage the proximal end of the expandable stylet and translate through the elongated shaft to expand the expandable end portion of the expandable stylet;

manipulating the rod to translate through the elongated shaft and correspondingly expanding the expandable end portion of the expandable stylet from an unexpanded first position to an expanded second position;

contacting the first outer surface of the expandable end portion of the expandable style with the inner wall portions of the first portion and the second portion of the elongated shaft to move the first portion and the second portion from an unexpanded third position to an expanded fourth position; and enlarging the hole during movement of the first portion and the second portion of the elongated shaft from the unexpanded third position to the expanded fourth position, wherein the first portion and second portion are disposed at a first distance from each other in the unexpanded third position, and the first portion and the second portion are disposed at a second distance from each other in the expanded fourth position, the second distance being greater than the first distance so as to enlarge the hole in the tissue.

12. The method of claim 11, wherein the elongated shaft includes adjacent the distal end thereof a second outer surface and a cutting portion provided on the second outer surface, and further comprising cutting the tissue and capturing the cut tissue in the elongated shaft.

13. The method of claim 11, further comprising suctioning the cut tissue out of the elongated shaft.

14. The method of claim 11, wherein the end portion of the expandable stylet includes at least a first portion and a second portion spaced apart from one another, and, during expansion of the expandable stylet, the first portion and the second portion of the end portion move farther apart from one another.

15. The method of claim 11, wherein the end portion of the expandable stylet includes at least a first portion and second portion, the first portion and the second portion of the end portion are spaced apart a maximum first distance when the end portion is in the unexpanded third position, and the first portion and the second portion of the end portion are spaced apart a maximum second distance when the end portion is in the expanded fourth position, the maximum second distance being greater than the maximum first distance.

16. The method of claim 11, wherein the elongated shaft includes adjacent the distal end thereof a second outer surface and a cutting portion provided on the second outer surface, the cutting portion being configured to cut the tissue.

17. The method of claim 16, wherein the cutting portion includes a band extending at least partially around the outer surface of the elongated shaft, the band including a plurality of spaced apart openings.

18. The method of claim 16, wherein the cutting portion includes a rasp surface configured to cut the tissue, and wherein rotation of the elongated shaft causes the rasp to cut the tissue.

* * * * *